United States Patent
Grant et al.

(10) Patent No.: US 10,080,583 B2
(45) Date of Patent: Sep. 25, 2018

(54) DILATOR FOR ACCESSING A JOINT SPACE

(71) Applicant: DePuy Mitek, LLC, Raynham, MA (US)

(72) Inventors: Bethany Grant, Scituate, MA (US); Joseph Algeri, Burlington, MA (US)

(73) Assignee: DEPUY MITEL, LLC, Raynham, MA (US)

(*) Notice: Subject to any disclaimer, the term of this patent is extended or adjusted under 35 U.S.C. 154(b) by 514 days.

(21) Appl. No.: 14/568,866

(22) Filed: Dec. 12, 2014

(65) Prior Publication Data
US 2016/0166278 A1    Jun. 16, 2016

(51) Int. Cl.
*A61B 17/88* (2006.01)
*A61B 17/34* (2006.01)
*A61B 17/02* (2006.01)
*A61B 17/32* (2006.01)

(52) U.S. Cl.
CPC ........ *A61B 17/3403* (2013.01); *A61B 17/025* (2013.01); *A61B 17/3417* (2013.01); *A61B 17/3421* (2013.01); *A61B 17/88* (2013.01); *A61B 17/320016* (2013.01); *A61B 17/3472* (2013.01); *A61B 17/3476* (2013.01); *A61B 17/8897* (2013.01); *A61B 2017/0275* (2013.01); *A61B 2017/3405* (2013.01); *A61B 2017/3454* (2013.01); *A61B 2017/3458* (2013.01)

(58) Field of Classification Search
CPC ............ A61B 17/8897; A61B 17/8852; A61B 17/8855; A61B 17/8858; A61B 17/1697; A61B 17/025; A61B 2017/0275; A61B 2017/025
See application file for complete search history.

(56) References Cited

U.S. PATENT DOCUMENTS

| | | |
|---|---|---|
| 3,659,607 A | 5/1972 | Banko |
| 4,362,161 A | 12/1982 | Reimels et al. |
| 4,456,010 A | 6/1984 | Reimels et al. |
| 4,723,546 A | 2/1988 | Zagorski |
| 4,787,378 A | 11/1988 | Sodhi |
| 4,927,421 A | 5/1990 | Goble et al. |
| 5,078,723 A | 1/1992 | Dance et al. |
| 5,129,901 A | 7/1992 | Decoste |
| 5,203,784 A | 4/1993 | Ross et al. |
| 5,306,301 A | 4/1994 | Graf et al. |

(Continued)

OTHER PUBLICATIONS

Badylak et al. "Do Iatrogenic Punctures of the Labrum Affect the Clinical Results of Hip Arthroscopy?" *YJARS*. (2011).

(Continued)

*Primary Examiner* — Samuel Hanna

(57) ABSTRACT

Systems and methods for accessing an interior space of a joint such as a hip joint in preparation for arthroscopic surgery are provided. In general, the described techniques utilize a joint access device having a handle and a dilator shaft and/or sheath coupled to a distal end of the handle. The device can be advanced over a guidewire inserted into a joint to a first position and the guidewire can be reversibly locked to the handle. The handle can be associated with an actuator configured to be actuated to cause the dilator shaft and/or sheath to advance distally toward a second position within the joint while simultaneously retracting the guidewire coupled to the handle.

12 Claims, 8 Drawing Sheets

(56) References Cited

U.S. PATENT DOCUMENTS

| | | |
|---|---|---|
| 5,320,610 A | 6/1994 | Yoon |
| 5,336,176 A | 8/1994 | Yoon |
| 5,380,333 A | 1/1995 | Meloul et al. |
| 5,573,511 A | 11/1996 | Yoon |
| 5,584,849 A | 12/1996 | Yoon |
| 5,586,991 A | 12/1996 | Yoon |
| 5,645,588 A | 7/1997 | Graf et al. |
| 5,697,944 A | 12/1997 | Lary |
| 5,697,947 A | 12/1997 | Wolf et al. |
| 5,843,108 A | 12/1998 | Samuels |
| 6,017,356 A | 1/2000 | Frederick et al. |
| 6,048,354 A | 4/2000 | Lawrence |
| 6,110,175 A | 8/2000 | Scholl |
| 6,200,274 B1 | 3/2001 | McNeirney |
| 6,270,501 B1 | 8/2001 | Freiberg et al. |
| 6,346,115 B1 | 2/2002 | Lawrence |
| 6,827,722 B1 | 12/2004 | Schoenefeld |
| 7,041,107 B2 | 5/2006 | Pohjonen et al. |
| 7,166,107 B2 | 1/2007 | Anderson |
| 7,207,995 B1 | 4/2007 | Vandewalle |
| 7,320,694 B2 | 1/2008 | O'Heeron |
| 7,341,596 B2 | 3/2008 | Heppler |
| 7,780,690 B2 | 8/2010 | Rehnke |
| 7,988,670 B2 | 8/2011 | Smith |
| 8,070,750 B2 | 12/2011 | Wenstrom, Jr. et al. |
| 8,202,318 B2 | 6/2012 | Willobee |
| 8,298,247 B2 | 10/2012 | Sterrett et al. |
| 8,298,284 B2 | 10/2012 | Cassani |
| 8,460,350 B2 | 6/2013 | Albertorio et al. |
| 8,591,544 B2 | 11/2013 | Jolly et al. |
| 8,591,578 B2 | 11/2013 | Albertorio et al. |
| 8,597,314 B2 | 12/2013 | McGhie |
| 8,617,167 B2 | 12/2013 | Weisel et al. |
| 8,663,324 B2 | 3/2014 | Schmieding et al. |
| 2003/0158521 A1 | 8/2003 | Ameri |
| 2006/0247649 A1* | 11/2006 | Rezach ............. A61B 17/7077 606/90 |
| 2008/0077146 A1 | 3/2008 | Pernsteiner et al. |
| 2008/0234717 A1 | 9/2008 | Bruszewski |
| 2009/0018655 A1 | 1/2009 | Brunelle et al. |
| 2009/0105754 A1 | 4/2009 | Sethi |
| 2009/0182340 A1 | 7/2009 | Nikolchev et al. |
| 2010/0249802 A1 | 9/2010 | May et al. |
| 2010/0268241 A1* | 10/2010 | Flom ................. A61B 17/3421 606/104 |
| 2011/0087258 A1 | 4/2011 | Sluss |
| 2011/0160755 A1 | 6/2011 | McGhie |
| 2011/0224742 A1* | 9/2011 | Weisel ............... A61B 17/0218 606/86 R |
| 2012/0046746 A1 | 2/2012 | Konicek |
| 2012/0157999 A1 | 6/2012 | Ochiai et al. |
| 2012/0239070 A1 | 9/2012 | Wijay et al. |
| 2013/0023907 A1 | 1/2013 | Sterrett et al. |
| 2013/0023927 A1 | 1/2013 | Cassani |
| 2013/0226239 A1 | 8/2013 | Altarac et al. |
| 2013/0317437 A1 | 11/2013 | Cleveland et al. |
| 2014/0074239 A1 | 3/2014 | Albertorio et al. |

OTHER PUBLICATIONS

Byrd et al. "Hip Arthroscopy for Labral Pathology: Prospective Analysis With 10-Year Follow-Up." *Arthroscopy*. 25.4(2009):365-368.

Ilizalitturi, Jr. et al. "Cartilage Injury Caused by Hip Scope." *ISHA Presentation*. (2011):e50-e51. (Abstract #13).

* cited by examiner

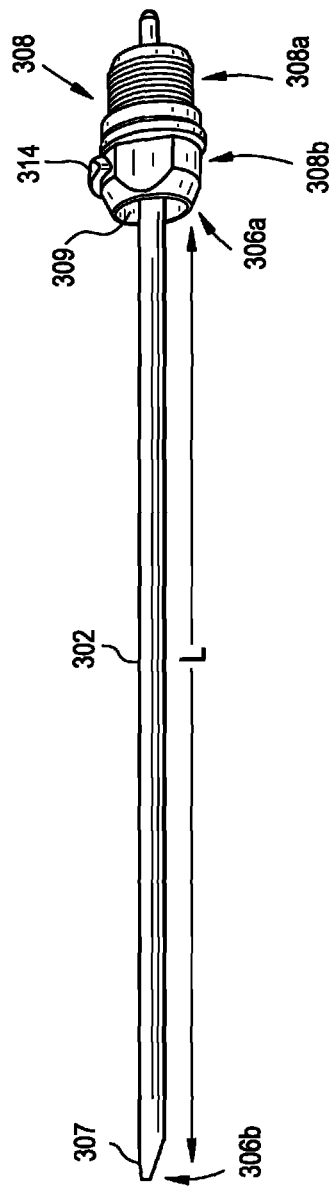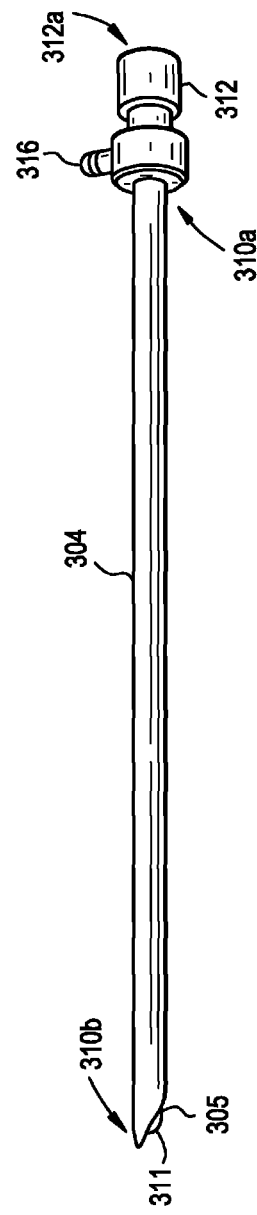
FIG. 3A
FIG. 3B

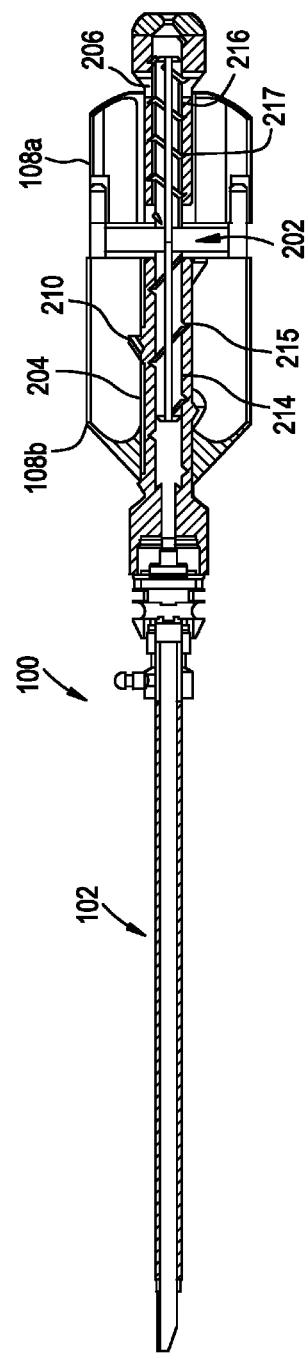
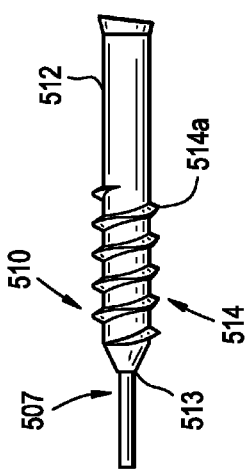
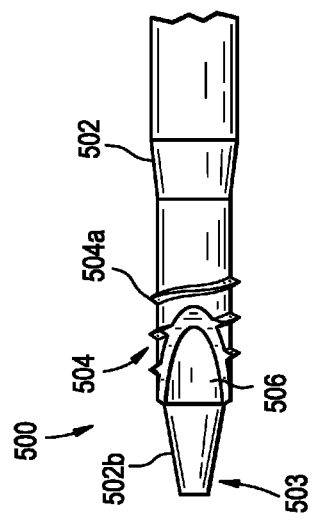

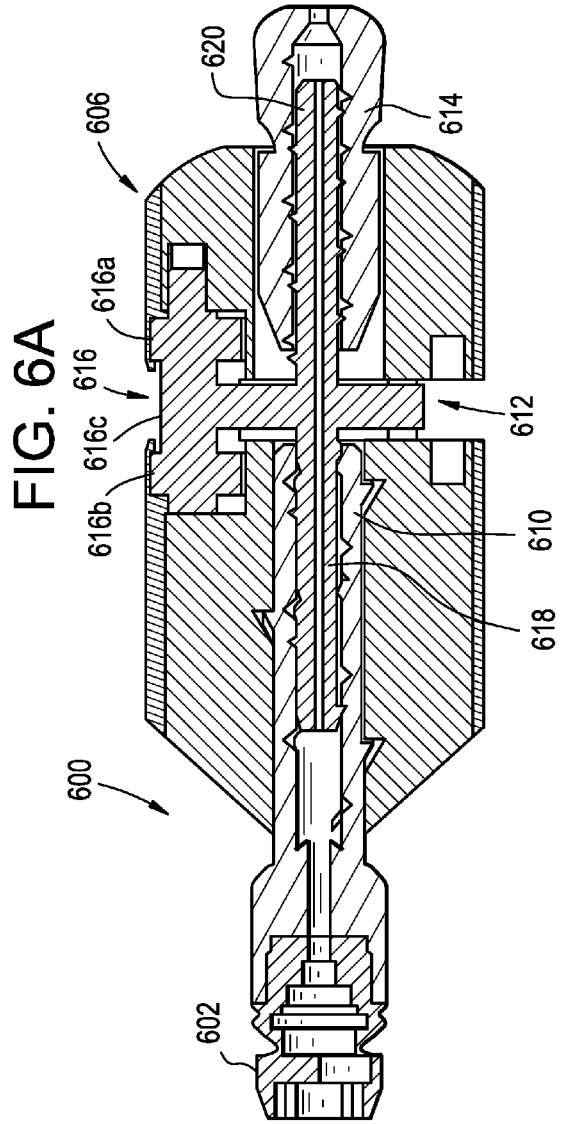
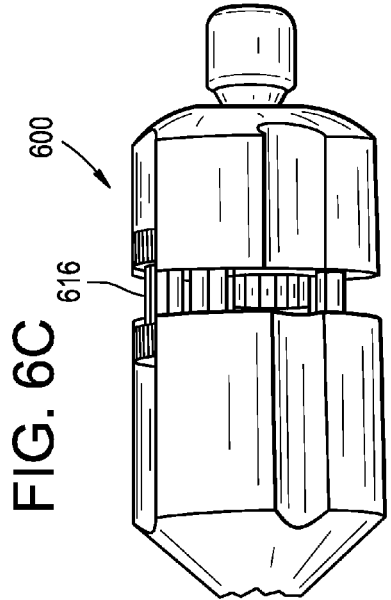
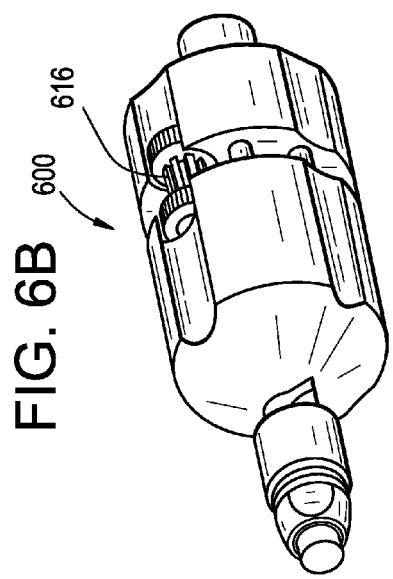

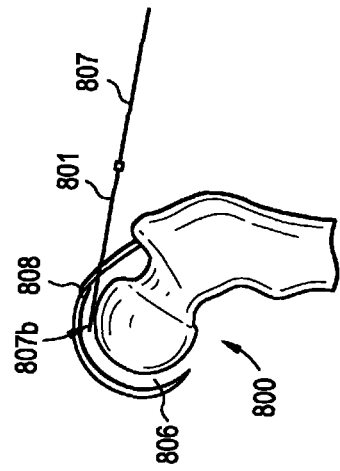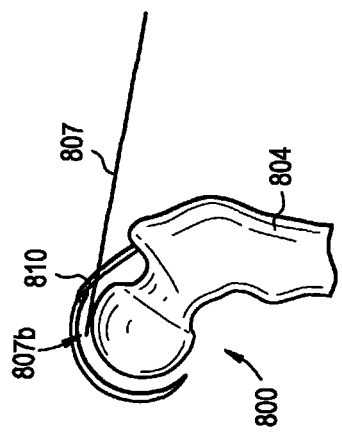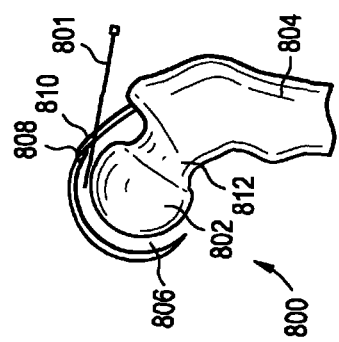

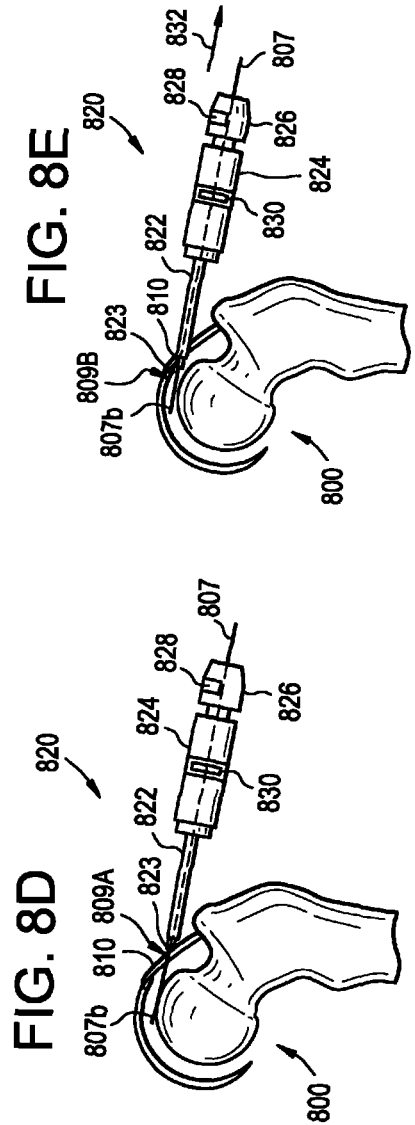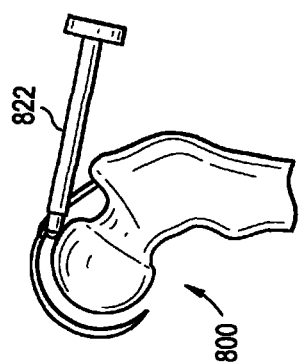

DILATOR FOR ACCESSING A JOINT SPACE

FIELD

The present disclosure relates to systems and methods for accessing the interior of a body and particularly to systems, methods, and devices for accessing the interior of a hip joint in preparation for arthroscopic surgery.

BACKGROUND

Many surgical procedures require access to the interior of a body. For example, to prepare a hip joint for an arthroscopic procedure, an access path must to be created to provide adequate access to the surgical site for an arthroscope and other instruments.

Some of the internal spaces in a body can be difficult to access. For example, a hip joint is considered to be more difficult to access and maneuver within than other joints for a number of reasons. Even at muscle relaxation during anesthesia, the joint space at the junction of the ball of the femoral head and the rim of the acetabulum maintains a strong vacuum force, sealed by the labrum and the capsular tissue (formed of muscular tissue and tendons constraining the joint). To allow surgical tools and instruments to access the joint space, it is required to apply force between the femur and the acetabulum to distract the joint. Once space is created in the joint, instruments are advanced through this thick, tough capsular tissue.

The conventional techniques for accessing internal spaces such as, for example, a hip joint space, involve inserting a needle, followed by a guidewire into tissue in the internal target space and then advancing a dilating tool over the guidewire into the target space. In this way, a dilator can be pushed over a guidewire into the hip capsule to access the hip joint. This technique can require the application of a significant force. Further, because of the difficultly in penetrating through the thick and tough capsular tissue into a narrow space within the hip joint, it can be challenging to advance the dilator toward the internal space without accidentally causing damage to articular cartilage. If an excessive force is used to advance the dilator toward the joint, iatrogenic damage can be caused by a tip of the dilator and/or by undesirably pushing the guidewire deeper into the capsule, such that the guidewire damages the articular surface of the acetabulum and/or femoral head.

Accordingly, there is a need for improved systems, methods, and devices for accessing interior body spaces such as an interior of a hip joint.

SUMMARY

In one aspect, a surgical method is provided that in some embodiments includes advancing a guidewire into a joint capsule, advancing a dilating instrument over the guidewire toward the joint capsule to a first position, the dilating instrument being coupled at a proximal end thereof to a handle such that the dilating instrument is capable of being moved relative to the handle reversibly locking the guidewire within the handle when the dilating instrument is in the first position, and actuating an actuator on the handle to cause the dilating instrument to advance distally from the first position toward a second position within the joint capsule and cause the guidewire to retract proximally simultaneously with advancing the dilating instrument toward the second position.

The method can vary in a number of ways. For example, the handle has the first and second couplings disposed therein. Actuating the actuator includes moving the first coupling to cause the dilating instrument to advance distally from the first position toward a second position within the joint capsule, and moving the second coupling to cause the guidewire to retract proximally simultaneously with advancing the dilating instrument toward the second position. Reversibly locking the guidewire can include locking the guidewire to the second coupling. The second coupling is configured to be operably coupled to the guidewire and to be moved by rotation.

The actuator includes a first engaging component operatively coupled to the first coupling and a second engaging component operatively coupled to the second coupling. The first and second engaging components can vary in a number of ways. For example, the first engaging component is operatively coupled to the first coupling via a first threaded connection. The second engaging component is operatively coupled to the second coupling via a second threaded connection. The first threaded connection includes a first thread having a first direction and the second threaded connection includes a second thread having a second direction opposite to the first direction.

Moving the first engaging component can cause the first coupling to move in a first direction and moving the second engaging component can cause the second coupling to move in a second direction that is opposite to the first direction.

In some aspects, a rate of retracting the guidewire is substantially the same as a rate of advancing the dilating instrument. In other aspects, a rate of retracting the guidewire is different than a rate of advancing the dilating instrument.

The joint capsule can be any capsule. In some aspects, the joint capsule is the hip joint capsule.

In some aspects, a distal tip of the dilating instrument has a cutting thread.

In other aspects, a surgical device is provided that includes a dilator assembly configured to be advanced over a guidewire through a tissue structure toward an interior space to a first position. The surgical device also includes a handle component, a first coupling disposed at least partially within the handle component, wherein the first coupling being configured to operatively couple to a proximal end of the dilator assembly and to move to cause the dilator assembly to advance distally from the first position toward a second position within the interior space, and a second coupling also disposed at least partially within the handle component. The second coupling is configured to engage a guidewire and to move to cause the guidewire to move proximally simultaneously with distal advancement of the dilator assembly toward the second position. The surgical device also includes an actuator operatively associated with the handle and including an actuating knob configured to be actuated to cause the first and second couplings to move.

The surgical device can vary in a number of ways. For example, the actuator includes first and second engaging components, and the actuating knob is configured to cause the first and second engaging components to move. The actuating knob and the first and second engaging components can be parts of the same component.

The first and second engaging components can vary in a number of ways. For example, the first engaging component is configured to be operatively coupled to the first coupling via a first threaded connection. The second engaging component is configured to be operatively coupled to the second coupling via a second threaded connection. In some embodiments, the second engaging component includes a gear system.

In some embodiments, a distal tip of the dilator assembly can have a cutting thread.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 3A is a side, perspective view of a dilator shaft in accordance with some embodiments;

FIG. 3B is a side, perspective view of a dilator sheath in accordance with some embodiments;

FIG. 4 is a side, cross-sectional view of a joint access device in accordance with some embodiments;

FIG. 5A is a schematic illustration of a tip of a dilator assembly in accordance with some embodiments;

FIG. 5B is another schematic illustration of a tip of a dilator assembly in accordance with some embodiments;

FIG. 6A is a side, cross-sectional view of a handle of a joint access device in accordance with some embodiments;

FIG. 6B is a side, perspective view of the handle of FIG. 6A;

FIG. 6C is another side, perspective view of the handle of FIG. 6A;

FIGS. 8A-8F are sequential schematic illustrations of a method of using a joint access device in accordance with some embodiments;

DETAILED DESCRIPTION

Figure 1:
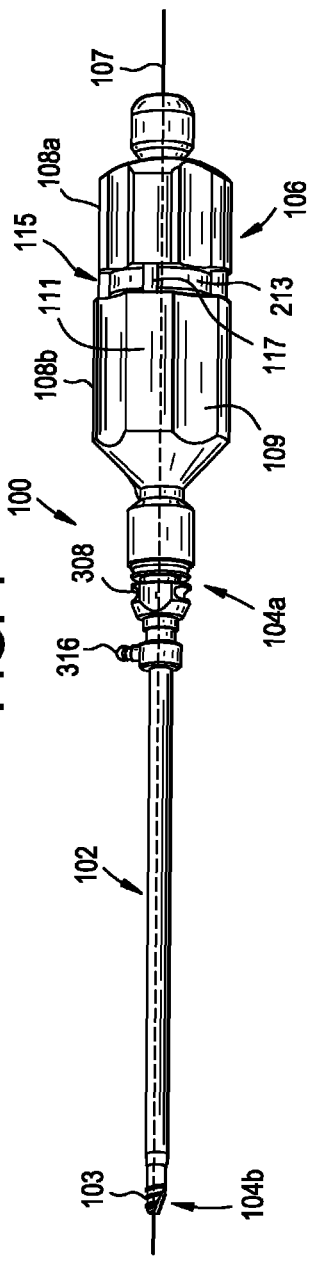
FIG. 1 is a side, perspective view of a joint access device in accordance with some embodiments.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to devices and methods for providing access to an interior space of a joint, such as a hip joint, to prepare the space for an arthroscopic surgical procedure. A device in accordance with some embodiments is a dilation instrument which can be advanced into the joint over a guidewire in a controlled manner such that the guidewire is retracted while the device is distally advanced. The control over a position of the guidewire during insertion of the dilator can prevent accidental damage to the joint and cartilage while creating of a path for surgical tools used in arthroscopic surgery.

Providing access to a hip joint in preparation for an arthroscopic procedure is a complex procedure which can be difficult to perform. Techniques for accessing a hip joint typically involve pushing a tool (e.g., dilator) over a guidewire. Because of its specific anatomy, the hip joint is difficult to access due to the narrow fit of the joint and the tough capsular tissue, and a surgeon may have to use a plunging action that generates force to advance the dilator into the hip capsule. Such an action can be difficult to control, and the surgeon may inadvertently continue to advance the dilator beyond the capsule even after the dilator reaches inside the hip capsule. This may lead to a tip of the dilator being pushed into the cartilage, thus causing unintentional damage to the articular surface of the femoral head and/or acetabulum. Additionally, the guidewire may be unintentionally advanced deeper into the hip joint while advancing the dilator, which can pin the guidewire between the tip of the dilator and the articular surface and, as a result, cause damage to the cartilage. In some cases, the guidewire can break in the joint and cause damage to the cartilage.

A device in accordance with some aspects disclosed herein allows a controlled advancement of a dilator into a joint space, such as the hip joint, while simultaneously retracting the guidewire and thus facilitates access to the hip joint in a minimally invasive manner with a significantly decreased risk of unintended damage to the hip joint. The device includes a dilator shaft or obturator and a handle removably coupled proximally of the dilator shaft. As explained further below, a dilator sheath can be used instead of or in addition to the dilator shaft. The dilator shaft and the handle define a lumen that can receive a guidewire inserted into the joint. An actuator associated with the handle is configured so as to advance the dilator shaft distally into the joint through the joint capsule, while simultaneously retracting proximally the guidewire, to create access for surgical tools and instruments to be used in a surgery on the joint.

The described devices, systems, and methods can be used in conjunction with different procedures, in a variety of different surgical contexts. For example, the devices, systems, and methods described herein are utilized in connection with hip arthroscopy procedures. The method includes inserting a guidewire into a hip joint, advancing a dilator device coupled to a handle over the guidewire to an outer surface of a capsule of a hip joint, engaging the guidewire to the handle, and advancing the dilator device distally, deeper into the joint capsule (e.g., the hip capsule), while at the same time retracting the guidewire proximally.

FIGS. 1 to 4 show a joint access device 100 in accordance with some aspects. As shown in FIG. 1, the joint access device 100 includes a dilator assembly 102 removably attached to a handle 106. The dilator assembly 102 and the handle 106 each define a respective lumen so that such lumens are in communication with each other and are configured to receive therein a guidewire 107 extending through the device 100. The handle 106 includes an actuator mechanism 202, shown in FIG. 2, that enables the dilator assembly 102 to be advanced distally over the guidewire 107 while simultaneously retracting the guidewire.

Figure 2:
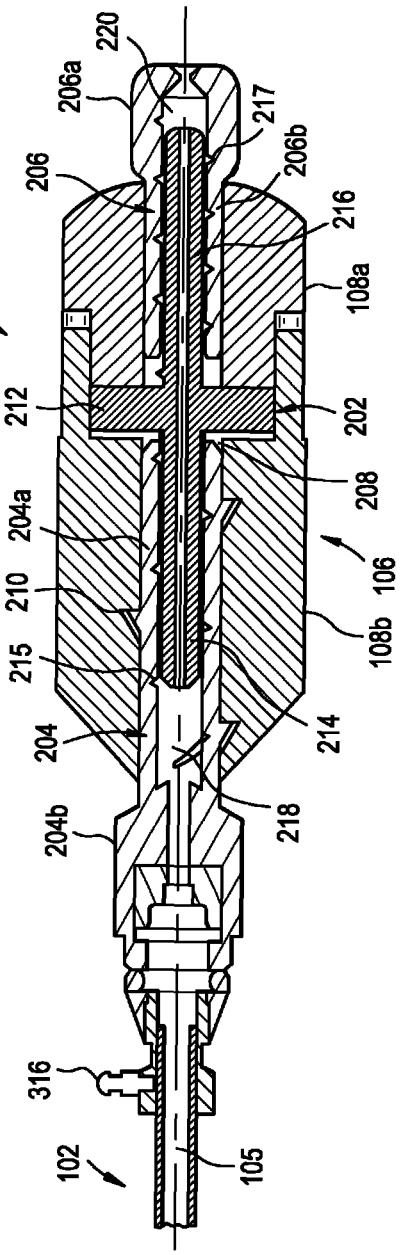
FIG. 2 is a side, cross-sectional view of a joint access device in accordance with some embodiments.

The dilator assembly 102 of the joint access device 100, which is configured to be advanced toward a joint, such as a hip joint, has proximal and distal ends 104a, 104b, and can take a form of an elongate dilation instrument of suitable size and shape effective to facilitate penetration of tissue with little or no trauma. As shown in FIG. 2, the dilator assembly 102 has an inner lumen 105 extending therethrough that is able to receive the guidewire 107 (shown in FIG. 1). The distal end 104b of the dilator assembly 102 can have a conical distal tip 103 having a reduced diameter, as shown in FIG. 1. In some embodiments, the distal tip 103 can have a thread formed thereon, as discussed in more detail below.

In the illustrated embodiments, the dilator assembly 102 can include a dilator shaft 302 (an example of which is shown in FIG. 3A) configured to couple to a distal end of the handle 106 and a dilator sheath 304 (an example which is shown in FIG. 3B) configured to receive therein the dilator shaft 302 and couple to the dilator shaft 302 and/or the handle 106.

The dilator shaft 302 is an elongate tubular instrument having proximal and distal ends 306a, 306b with a lumen formed therethrough. The lumen of the dilator shaft 302 can be the lumen 105 of the dilator assembly 102 shown in FIG. 2 configured to receive therein the guidewire 107. As shown in FIG. 3A, in the illustrated embodiment, the dilator shaft 302 includes a hub 308 at the proximal end 306a thereof. The hub 308 also has a lumen extending therethrough configured to receive therein the guidewire 107 such that the device 100 is also able to receive the guidewire 107 therethrough along its entire longitudinal axis.

As shown in FIG. 3A, the hub 308 includes a distal portion 308b having an inner cavity 309 that receives and couples to the proximal end 306a of the dilator shaft 302. The hub 308 can also include a proximal portion 308a configured to reversibly mate with the handle 106. As shown in FIG. 3A, the proximal portion 308a of the hub 308 can be externally threaded so that the hub 308 can threadedly mate with internal threads (not shown) of the handle 106.

A shown in FIG. 3A, a distal tip 307 of the distal end 306b of the dilator shaft 302 is distally tapered to facilitate advancement of the dilator shaft 302 into tissue. In some embodiments, the distal end 306b of the dilator shaft 302 can include one or more threads and/or other features formed thereon that additionally facilitate engagement of the dilator shaft with tissue, as discussed in more detail below.

As shown in FIG. 3B, the dilator sheath 304 is an elongate tubular instrument having proximal and distal ends 310a, 310b. The dilator sheath 304 is hollow such that a lumen 305 extending therethrough can receive therein the dilator shaft 302. Thus, the dilator sheath 304 has an inner diameter slightly larger than an outer diameter of the dilator shaft 302 so that the dilator sheath 304 can be advanced over the dilator shaft 302 and can be removably coupled to both the dilator shaft 302 and the handle 106. The dilator sheath 304 has a hub 312 at a proximal end thereof that is configured to attach the dilator sheath 304 to the dilator shaft 302 and the handle 106.

By way of a non-limiting example, a distal tip 311 of the distal end 310b of the dilator sheath 304 is distally tapered at one side, as shown in FIG. 3B. However, one skilled in the art will appreciate that the described embodiments are not limited to any specific configuration of the distal end of the dilator sheath 304. For example, the distal tip 311 can be rounded or shaped otherwise. Furthermore, in some embodiments, a distal tip of one or both of the dilator sheath and the dilator shaft can include one or more threads formed thereon, as discussed in more detail below.

The dilator sheath 304 can engage with the dilator shaft 302 in a number of ways, all of which are well known to those skilled in the art. Exemplary connections include threaded conversions, spring loaded connections, and J-lock connections. By way of an example, in the illustrated embodiment, the cavity 309 defined within the distal portion 308b of the hub 308 of the dilator shaft 302 removably receives therein a proximal end 312a of the hub 312 of the dilator sheath 304, enabling the hub 312 to mate with the hub 308 using any suitable locking mechanism. For example, the distal portion 308b of the hub 308 can include therein a spring (not shown) that biases components of the proximal end 312a of the hub 312 to join the hub 308 to thus join the dilator sheath 304 with the dilator shaft 302.

As shown in FIG. 3A, the distal portion 308b of the hub 308 includes a push button 314 which is biased by the spring to a position in which the button 314 extends above the outer surface of the distal portion 308b when the proximal end 312a of the hub 312 is slidably received in the cavity 309. To separate the dilator sheath 304 from the dilator shaft 302 and the proximal handle 106, the button 314 is activated (e.g., pushed down). Further, as shown in FIGS. 1, 2, and 3B, the dilator sheath 304 includes at the proximal end 310a thereof a lock 316 which can be a pin, screw, or any other attachment element configured to reversibly lock the dilator sheath 304 to the dilator shaft 302 so that they do not move with respect to each other. It should be appreciated that the dilator sheath 304 can engage with the dilator shaft 302 in any suitable manner, as the described embodiments are not limited in this respect.

In use, when the dilator assembly 102 is operated to provide access to a joint space, the dilator shaft 302 can extend through the inner lumen 305 of the dilator sheath 304. The cavity 309 of the distal portion 308b of the hub 308 can receive therein the proximal end 312a of the hub 312 such that the entire hub 312 or a portion thereof (e.g., in the illustrated embodiment, a portion of the hub 312 located proximally to the lock 316) is inserted into the cavity 309. In some embodiments, the dilator shaft 302 can extend through the inner lumen 305 of the dilator sheath 304 so that the distal tip 307 of the dilator shaft 302 protrudes distally beyond the distal end 311 of the dilator sheath 304. This allows for a smooth transition between the distal ends of the dilator shaft 302 and dilator sheath 304, which can help reduce trauma to tissue as it is being penetrated by the dilator assembly 102.

The dilator sheath 304 can be mated to the dilator shaft 302 before or after the dilator shaft 302 is coupled to the handle 106. The dilator assembly 102 can be mated to the handle 106, for example, by threadedly engaging the proximal portion 308a of the hub 308 with the handle via a coupling 204, as disused in more detail below.

It should be appreciated that, while in some embodiments the dilator assembly 102 can include both the dilator sheath 304 having the dilator shaft 302 extending therethrough, in other embodiments, the dilator assembly 102 can include either a dilator sheath or a dilator shaft that can have any suitable configuration and can be configured to removably engage with the handle 106 in any suitable manner. For example, the dilator assembly 102 can include only the dilator shaft 302 that can be used to penetrate tissue in the joint.

Regardless of whether the dilator assembly 102 includes one or both of the dilator sheath 304 and the dilator shaft 302, the dilator assembly 102 can include components having any suitable size and configuration. For example, in some embodiments, a working length L (shown by way of example in FIG. 3A) of the elongate portion of one or both of the dilator shaft 302 and the dilator sheath 304 is from about 40 mm to about 200 mm. In one embodiment, the length L is about 175 mm, which can be a length sufficient for penetration into a hip capsule of patients with a high body mass index (BMI). In one embodiment, an outer diameter of one or both of the dilator shaft 302 and the dilator sheath 304 is from about 4 mm to about 8 mm. However, one skilled in the art will understand that the dilator shaft 302 and the dilator sheath 304 can have any suitable diameter selected such that the inner diameter of the dilator sheath 304 is slightly larger than the outer diameter of the dilator shaft 302 so that the dilator shaft 302 can be inserted to fit snugly within the dilator sheath 304.

The portions of the handle 106 can have a variety of configurations. By way of example, as shown in FIGS. 1 and 2, the handle 106 is in the form of an elongate body having a generally cylindrical shape with proximal and distal portions 108a, 108b (one or both of which can be tapered), first and second couplings 204, 206 extending within the handle 106, and an actuator mechanism 202 disposed between the first and second couplings 204, 206. The handle 106 is sized such that it can be conveniently held by the operator and such that any actuators accessible on the outer surface of the handle 106 can be easily manipulated when the joint access device is in use. The handle is configured to be held using both hands of the operator. In some embodiments, however, the handle is configured to be held and operated using one hand.

The proximal and distal portions 108a, 108b of the handle 106 are operatively coupled to each other. The handle 106 is configured to be held by a surgeon to operate the joint access device 100 and advance the dilator assembly 102 into a joint. The outer surface of the handle 106 can include various features that facilitate grip by the operator. In the example of FIG. 1, the handle 106 includes surface features, such as longitudinal grooves 109, longitudinal ridges 111 disposed between the longitudinal grooves 109, and other features. Furthermore, the handle 106 can be associated with one or more actuators, such as knobs, dials, buttons, levers, locks, screws, and other actuators and/or control components configured to actuate mechanisms associated with the handle. It should be appreciated that the device 100 can include a handle having any other suitable surface features.

As shown in FIG. 2, the handle 106 has a lumen 208 extending therethrough such that the handle 106 is cannulated. The lumen 208 is axially aligned along a longitudinal axis of the joint access device 100 and at least partially receives therein the first and second couplings 204, 206.

The first coupling 204 is disposed within the distal portion 108b of the handle 106. As shown in FIGS. 2 and 4, the first coupling 204 threadedly engages with an inner surface of the lumen 208 via an external thread 210 formed on an outer surface of the first coupling 204. The external thread 210 is configured to engage with a complementary internal thread formed in the distal portion 108b on an inner surface of the lumen 208. The first coupling 204 has a proximal portion 204a disposed at least partially within the lumen 208 and a distal portion 204b extending distally beyond a distal end of the distal portion 108b. As shown in FIG. 2, the distal portion 204b of the first coupling 204 is coupled to the dilator assembly 102. When the joint access device 100 is operated to access an internal space of a joint, the first coupling 204 is moved distally such that it further protrudes from the distal end of the distal portion 108b of the handle 106.

The second coupling 206 is disposed proximally of the first coupling 204, within the proximal portion 108a of the handle 106. As shown in FIGS. 2 and 4, the second coupling 206 is slidably disposed within the lumen 208. In some aspects, the second coupling 206 has an external thread (not shown) formed thereon so that it can be threadedly disposed within the lumen 208. As shown, the second coupling 206 includes a proximal portion 206a having an enlarged diameter and extending proximally beyond a proximal end of the proximal portion 108a of the handle 106. A distal portion 206b of the second coupling 206 can be disposed substantially entirely within the lumen 208. When the joint access device 100 is operated, the second coupling 206 is moved proximally such that it further protrudes from the proximal end of the proximal portion 108a of handle 106.

As discussed above, a guidewire, such as the guidewire 107 shown in FIG. 1, can be reversibly locked to the handle 106. In the illustrated embodiment, the second coupling 206 includes a mechanism configured to reversibly attach the guidewire 107 thereto. For example, the second coupling 206 can include a lock component (not shown) which is configured to lock the guidewire 107 disposed within the handle 106 so that the guidewire 107 moves together with the second coupling 206. The locking component can be a screw, lock, pin, clamp, or any other fastening mechanism disposed in any location on the second coupling 206. It should be appreciated that the guidewire 107 can be reversibly locked to the second coupling 206 using any suitable mechanism. The mechanism can be operated via an actuator (e.g., a push button, lever, dial, knob, switch, etc.) that can at least partially protrude from the outer surface of the handle 106 such a surgeon can easily and conveniently lock or unlock the guidewire 107 while holding the handle 106 to operate the joint access device 100

The actuator mechanism 202 can vary in a number of ways. In the illustrated embodiment, as shown in FIG. 2, the actuator mechanism 202 includes an actuating knob 212, a first engaging component 214 extending distally from the actuating knob 212, and a second engaging component 216 extending proximally from the actuating knob 212.

As shown in FIG. 1, the actuating knob 212 is associated with the handle 106 such that at least a manipulation portion 213 of the actuating knob 212 can protrude from or be accessible from an outer surface of the body 108 and can be configured to be moved (e.g., rotated or otherwise moved) by a surgeon's hand. As shown, the actuator mechanism 202 is disposed within the body of the handle 106 such that the manipulation portion 213 protrudes from an opening 115 formed transversely between the proximal and distal portions 108a, 108b of the body of the handle 106. As shown in FIG. 1, the proximal and distal portions 108a, 108b of the handle 106 are connected by one or more arms or prongs 117 extending therebetween across the opening 115. In the illustrated embodiment, the proximal and distal portions 108a, 108b of the handle 106 are separate components fixedly connected by the arms 117 and any other features (not shown). Alternatively, the proximal and distal portions 108a, 108b are formed integrally, with the opening 115 formed therebetween.

The manipulation portion 213 of the actuating knob 212 can include exterior surface features (e.g., grooves, ridges, recesses, textures, or any other features) that facilitate grasping and movement thereof by the hand of the operator. In the illustrated embodiment, the actuating knob 212 is configured as a dial or thumbwheel that can be rotated in a clockwise or counter-clockwise direction to thereby move (e.g., advance or retract) the dilator assembly 102 while simultaneously retracting the guidewire 107. However, any other configuration can be utilized additionally or alternatively, as the described techniques are not limited to any specific configuration and the matter of operation of the actuating knob 212.

The actuator 202 is configured so that movement of the actuating knob 212 causes both the first and second engaging components 214, 216 to move at the same time. In some aspects, the first and second engaging components 214, 216 are formed integrally with the actuating knob 212 such that they are parts of the same component. Thus, in such aspects, the actuator mechanism 202 is a single component configured to be operated to advance the dilator assembly while simultaneously retracting the guidewire. However, in other aspects, one or both of the first and second engaging components 214, 216 can be formed separately from the actuator 202 and can be configured to operatively engage the actuating knob 212 in a suitable manner.

In the illustrated embodiment, the first and second engaging components 214, 216 are configured to engage (e.g., threadedly) with the first and second couplings 204, 206 so that movement of the first and second engaging components 214, 216, caused by movement of the actuating knob 112, causes the first and second couplings 204, 206, respectively, to move in opposite directions.

As shown in FIG. 2, the first coupling 204 includes a first lumen 218 extending therethrough that is configured to receive the first engaging component 214 operatively coupled to the first coupling 204. The first engaging component 214 can extend along a portion or substantially the entire length of the first coupling 204. As also shown in FIG. 2, the first engaging component 214 includes an external thread 215 formed on at least a portion of the outer surface thereof, with the thread 215 having a first direction (e.g., it can be a right-handed thread). The external thread 215 is configured to engage with a complementary internal thread formed in the inner sidewall of the lumen 218 extending through the first coupling 204. The thread 215 can be a single, continuous thread, as in the illustrated embodiment, that extends around the first engaging component 206. In some embodiments, as one skilled in the art will appreciate, a plurality of threads can be formed.

Similarly, the second coupling 206 includes a second lumen 220 extending therethrough that is configured to receive the second engaging component 216 operatively coupled to the second coupling 206. The second engaging component 216 extends along a portion or substantially the entire length of the second coupling 206. The second engaging component 216 includes an external thread 217 formed on at least a portion of the outer surface thereof and having a second direction (e.g., it can be a left-handed thread) that is opposite to the first direction of the thread 215 formed on the first engaging component 206. The external thread 217 is configured to engage with a complementary internal thread formed in the inner sidewall of the lumen 220 extending through the second coupling 206. The thread 217 can be a single, continuous thread, as in the illustrated embodiment, that extends around the second engaging component 216. In some embodiments, as one skilled in the art will appreciate, a plurality of threads can be formed.

Because the threads 215, 217 extend in opposite directions, moving the actuating knob 212 causes the first and second engaging components 214, 216 to simultaneously move (e.g., rotate) in opposite directions such that the first and second couplings 204, 206 also move simultaneously. The actuating knob 212 is configured to rotate about an axis that is parallel to the longitudinal axis of the joint access device 100, whereas the first and second engaging components 214, 216 mated to the actuating knob 212 rotate about respective longitudinal axes thereof.

The threads 215, 217 can have any suitable configuration and dimensions. For example, the thread 215 can be a right-handed thread that winds in a clockwise direction and requires a right-hand or clockwise rotation for a forward advancement of a shaft having the thread formed thereon into a tight space. The thread 217 can be a left-handed thread that winds in a counter-clockwise direction and requires a left-hand or counter-clockwise rotation for a forward advancement of a shaft having that thread formed thereon. A pitch of one or both of the threads 215, 217 can be configured such that about 720 degrees of rotation is equivalent to about 8 millimeters (mm) of travel through the hip capsule. For example, the pitch of one or both of the threads 215, 217 is about 4 mm. As used herein, the pitch of a thread is defined as a distance along an axis of a thread between consecutive crests which are surfaces of the thread that join flanks of the thread and are farthest from a surface from which the thread projects.

It should be appreciated that one of both of the threads 215, 217 can have any suitable pitches, which can be the same or different pitches. For example, in some cases, the thread pitch varies from about 0.5 mm to about 8 mm. Unless specifically stated or obvious from context, as used herein, the term "about" is understood as within a range of normal tolerance in the art.

In use, rotation of the actuating knob 212 causes the first and second engaging components 214, 216 to simultaneously move in a turnbuckle-like manner. Because the first and second engaging components 214, 216 are operatively coupled to the first and second couplings 204, 206, respectively, the movement of the first and second engaging components 214, 216 causes the first and second couplings 204, 206 to move as well. The first coupling 204 is moved distally to thereby cause the dilator assembly 102 distally coupled thereto to advance distally, and the second coupling 206 is substantially simultaneously moved proximally to thereby cause the guidewire 107 locked thereto to also move proximally. Thus, the joint access device 100 allows access of an internal space of a joint (e.g., a hip joint) in a simple, efficient, and controlled manner, by actuation of the actuator mechanism 202.

The guidewire 107, which is retracted substantially simultaneously with advancement of the dilator assembly 102, can be retracted at the same or different rate than a rate of distally advancing the dilator assembly 102. In embodiments in which the guidewire 107 is retracted at the same rate that the dilator assembly 102 is advanced, the threads 215, 217 formed on the first and second engaging components 214, 216, respectively, have the same pitch. In other embodiments, in which the guidewire 107 is retracted at a rate different than a rate at which the dilator assembly 102 is advanced, the threads 215, 217 have different pitches. Thus, the pitches of the threads 215, 217 can be selected based on a desired rate of retracting the guidewire relative to a rate of advancement of the dilator assembly.

As mentioned above, a distal end of a dilator assembly of a joint access device described herein can include features that facilitate engagement of the dilator assembly with tissue and its advancement into the joint. For example, in some embodiments, a distal end of a dilator shaft and/or a dilator sheath of the dilator assembly can include threads.

FIGS. 5A and 5B illustrate additional embodiments of a distal end of the dilator assembly of the joint access device, such as the joint access device 100. By way of a non-limiting example, FIG. 5A illustrates an example of a distal end of a dilator assembly including a dilator sheath with a dilator shaft received therein. FIG. 5B illustrates an example of a dilator shaft. It should be appreciated that in embodiments in which the dilator assembly includes, in addition to the dilator shaft, the dilator sheath (e.g., the dilator sheath 304 in FIG. 3B) that can be advanced over and removably coupled to the dilator shaft, additionally or alternatively, a distal end of the dilator sheath can include the features shown in connection with FIGS. 5A and 5B.

As shown in FIG. 5A, a distal end 500 of a dilator assembly includes a dilator sheath 502 having a generally conical, distally tapered dilator tip 503 of a dilator shaft 502b protruding therefrom. The dilator sheath can have a thread 504 formed on an outer surface thereof that facilitates introduction of the dilator sheath 502 into a joint as the dilator sheath 502 with the dilator shaft 502b are rotatably advanced distally. In this example, the dilator tip 503 of the dilator shaft 502b is free of the thread 504. However, in some aspects, the dilator tip 503 can additionally or alternatively be threaded. The thread 504 can be a helical cutting thread and can include any suitable number of segments or windings extending about the outer surface of the distal end 500, and three segments 504a are shown in FIG. 5A by way of example only.

The distal end 500 can include any other surface features that help to safely and efficiently advance the dilator sheath 502 with the dilator shaft 502b into a joint. For example, FIG. 5A shows that one side of the distal end 500 includes a cutout window 506 to provide visualization of arthroscope into joint. The cutout window 506 can be tapered distally or it can have any suitable shape.

FIG. 5B illustrates another embodiment of a distal end 510 of a dilator shaft 512 in accordance with some embodiments. As discussed above, the dilator shaft 512 can be cannulated so that it can receive therein a guidewire 507, shown in FIG. 5B to protrude distally beyond a distal tip 513 of the distal end 510. Similar to the distal end 500 of the sheath 502, the distal end 510 of the dilator shaft 512 includes a continuous thread 514 formed around an outer surface thereof in a helical or other pattern. The thread 514 can include any number of windings 514a which can have sharp edges that help to cut through and grip tissue.

The threads 504, 514 shown in FIGS. 5A and 5B, or any other threads that can be formed on a distal end of the dilator and/or sheath assembly, can have any suitable configuration and dimensions. It should be appreciated that one of both of the threads 504, 514 can have any suitable pitch, which can be the same or different pitches. In some aspects, the pitch of one or both of the threads 504, 514 can be selected such that about 720 degrees of rotation is equivalent to about 8 millimeters (mm) travel through the hip capsule. One skilled in the art will appreciate that the pitches can vary from about 0.5 mm to about 10 mm, or within any other suitable range(s). For example, the pitch of one or both of the threads 504, 514 can be about 4 mm.

In some aspects, a pitch of a thread formed at a distal end of the dilator assembly (e.g., the threads 504, 514) matches a pitch of a thread formed on one or both of the first and second engaging components of the actuator mechanism, such as the threads 215, 217 formed on the first and second engaging components 214, 216 (FIGS. 2 and 4). This allows advancing the dilator assembly distally into the internal space of the joint at a rate that is the same or substantially the same as a rate at which the guidewire is retracted.

In some aspects, a major diameter of one or both of the threads 504, 514 (or any other threads used in conjunction with the described joint access device) is from about 2.5 mm to about 7 mm. In one embodiment, the major diameter can be about 4.5 mm. A ratio between major and minor diameters of the threads is any suitable value, for example, from about 1.1 mm to about 2 mm. In one embodiment, the ratio may be about 1.65 mm, which in some cases may provide for enhanced engagement with the hip capsule. It should be appreciated, however, that the pitch, major and minor diameters and their ratio(s), and any other characteristics of the threads formed on the distal tip of the dilator assembly can have any suitable values.

FIGS. 6A to 6C illustrate an alternative embodiment of a handle 606 of a joint access device 600. Similar to the handle 106 of the joint access device 100 (FIGS. 1, 2, and 4), the handle 606 is removably coupled proximally to a dilator assembly 602.

The dilator assembly 602 is similar to the dilator assembly 102 of the joint access device 100 and is not described herein.

Similarly, as shown in FIG. 6A, the handle 606 can include components similar to the components included in the handle 106 of FIGS. 1, 2, and 4. Thus, the handle 606 has a generally cylindrical shape, first and second couplings 610, 614, and an actuator mechanism 612 disposed between the first and second couplings 610, 614. The actuator mechanism 612 includes an actuating member 616, a first engaging component 618 disposed distally of the actuating member 616, and a second engaging component 620 disposed proximally of the actuating member 616. As shown in FIGS. 6A-6C, the actuating member 616 includes a proximal portion 616a, a distal portion 616b, and a middle portion 616c disposed between the proximal and distal portions 616a, 616b. The proximal, distal, and middle portions 616a, 616b, 616c can be formed integrally or they can be separate components coupled in a suitable manner.

In the illustrated embodiment, the middle portion 616c of the actuating member 616 protrudes from the outer surface of the body of the handle 600, for example at least on the top surface as shown in FIGS. 6B and 6C. The middle portion 616c can be a knob, dial, thumbwheel, or any other actuator that can include features (e.g., ridges shown in FIGS. 6B and 6C) that help to grip and move the actuating member 616. The middle portion 616c can be configured to be actuated (e.g., rotated) by a surgeon to operate the joint access device 600 in a manner similar to the operation of the joint access device 100 discussed above and further in more detail below in connection with FIGS. 8A-8E. For example, it can be rotatable about an axis transverse to a longitudinal axis of the joint access device 600, or in any other manner. It should be appreciated that the handle 606 can have any configuration and the actuator mechanism 612 can include an actuating member having any suitable configuration.

Figure 7:
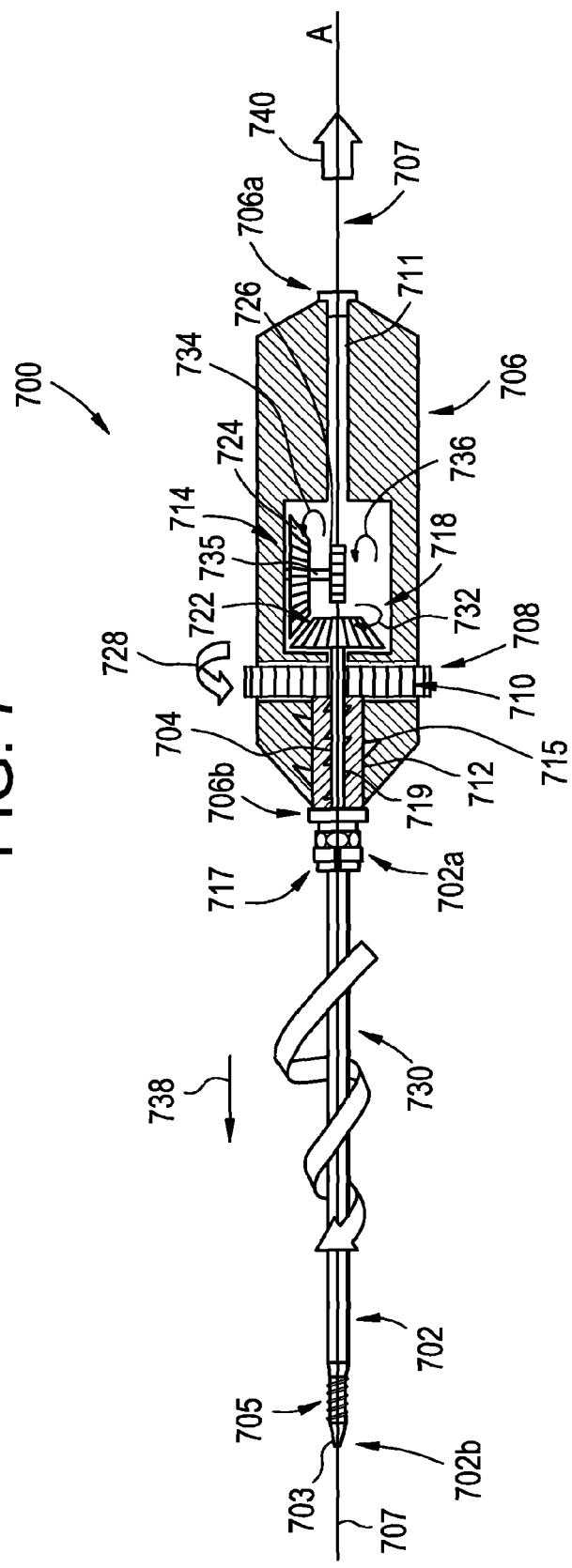
FIG. 7 is a side view of a joint access device including an actuator having a gear system, in accordance with some embodiments.

FIG. 7 illustrates another embodiment of a joint access device 700 used to access an interior space of a joint in accordance with some embodiments. As shown, the joint access device 700 includes a dilator assembly 702 and a handle 706 removably coupled proximally thereto. Similar to joint access device 100, the joint access device 700 is cannulated so that it can receive therein a guidewire 707 extending through an entire length of thereof.

The dilator assembly 702 can have a variety of configurations. In the illustrated embodiment, the dilator assembly 702 includes a dilator sheath advanced over and removably coupled to a dilator shaft (not shown). However, as one skilled in the art will appreciate, the dilator assembly 702 can include only the dilator shaft, as embodiments are not limited to a specific configuration of the dilator assembly 702.

As shown in FIG. 7, the dilator assembly 702 is an elongate tubular member having proximal and distal ends 702a, 702b. A distal tip 703 of the dilator assembly 702 can be distally tapered and can have a thread 705 formed about an outer surface thereof that facilitates advancement of the dilator assembly 702 into tissue. The dilator assembly 702 is able to be coupled to the distal portion of the handle 706 in a suitable manner. For example, the proximal end 702a of the dilator assembly 702 can be configured to be inserted into the distal end 706b of the handle 706 to threadedly or otherwise engage therewith. Further, as shown in FIG. 7, the dilator assembly 702 is able to be reversibly locked to the handle 706 via a locking component 717 which can have any suitable mechanism. Regardless of the manner in which it engages with the handle 706, the dilator assembly 702 is operatively coupled with a first coupling 712 of the handle 706 such that moving the first coupling 712 distally causes the dilator assembly 702 to advance distally, as discussed in more detail below.

The handle 706 can also have a variety of configurations. As shown in FIG. 7, the handle 706 is an elongate body having proximal and distal ends 706a, 706b, and a lumen 711 extending between the proximal and distal ends 706a, 706b. The lumen 711 can be formed within the handle 706 coaxially with a longitudinal axis A thereof and can have different cross-sectional diameters or widths along the longitudinal axis.

As shown in FIG. 7, the lumen 711 has disposed therein an actuator mechanism 708 having an actuating knob 710, a first coupling 712 disposed distally of the actuating knob 710, and a second coupling 714 disposed proximally of the actuating knob 710. The portions of the lumen 711 including the above features can have dimensions suitable to house the features therein. For example, the portion of the lumen 711 disposed distally of the actuating knob 710 is sized to receive the first coupling 712, and the portion of the lumen 711 disposed proximally of the actuating knob 710 has a larger diameter suitable to receive the second coupling 714 within the lumen 711. As also shown in FIG. 7, a portion of the lumen 711 disposed closer to the proximal end 706a of the handle 706 has a decreased diameter configured to receive therein the guidewire 707.

The first and second couplings 712, 714 are coupled to the actuator mechanism 708 and configured such that activation of the actuator mechanism 708 (e.g., by rotating the actuating knob 710) causes the first and second couplings 712, 714 to move in opposite directions. In the illustrated embodiment, the first coupling 712 is configured as an elongate tubular member that is coupled to the handle 706 via an external thread 715 formed around an outer surface of the first coupling 712. The external thread 715 is configured to engage with an internal thread (not shown) formed in the handle 706. The second coupling 714 includes a system of gears coupled to the actuator mechanism 708 and to the guidewire 707, as described in more detail below.

As shown in FIG. 7, in the illustrated embodiment, the actuator mechanism 708 can include a first engaging component 704 extending distally from the actuating knob 710, and a second engaging component 718 disposed proximally from the actuating knob 710. In the illustrated embodiment, the first and second engaging components 704, 718 are configured to engage with the first and second couplings 712, 714, respectively, so that movement of the first and second engaging components 704, 718, caused by movement of the actuating knob 710, causes the first and second couplings 712, 714, respectively, to move so that the dilator shaft 702 and the guidewire 707 move in opposite directions.

The first engaging component 704 is configured as an elongate tubular member distally coupled to or integrally formed with the actuator mechanism 708 such that the first engaging component 704 rotates and advances distally when the actuator mechanism 708 is activated. As shown in FIG. 7, the first engaging component 704 is at least partially disposed within the first coupling 712 and it is configured to engage with the first coupling 712 so that movement of the first engaging component 704 causes the first coupling 712 to move. In the illustrated embodiment, the first engaging component 704 is threadedly coupled with the first coupling 712 via an external thread 719 formed about an outer surface of the first engaging component 704. The external thread 719 is configured to engage with a complementary internal thread formed in the first coupling 712. In FIG. 7, the first engaging component 704 extends throughout the entire length of the first coupling 712. However, it should be understood that the first engaging component 704 can extend throughout a portion of the first coupling 712.

In the illustrated embodiment, when the engaging component 704 engaged or integrally formed with the actuator mechanism 708 is rotated, this causes the first coupling 712 to rotate and advance distally. The first coupling 712 can be moved distally such that it protrudes from the distal end 706b of the handle 706. Because the first coupling 712 is coupled distally to the dilator assembly 702, distally advancing the first coupling 712 causes the dilator assembly 702 to also advance distally. It should be appreciated that the first coupling 712 can have any suitable configuration. Furthermore, one skilled in the art will appreciate that the first coupling 712 can be coupled to the handle 706 and can be engaged with the first engaging component 704 in any suitable manner.

The second coupling 714 can also have a variety of configurations. In the illustrated embodiment, the second coupling 714 includes a gear system 718, also referred to as a second engaging component, encompassing a system of gears. The gear system 718 includes a series of beveled gears 722, 724, and a coaxial gear 726 that are configured to transfer a movement (e.g., rotation) of the actuating knob 710 about the longitudinal axis A of the handle 706 to a proximal translational movement of the guidewire 707 in the direction of arrow 740 along the longitudinal axis A of the handle 706. As shown in FIG. 7, the beveled gear 722 is disposed proximally of and is coupled to actuator knob 710 so that it rotates coaxially in a direction 732 about longitudinal axis A. The beveled gear 724 is proximal of and operatively coupled to beveled gear 722 and is configured to rotate about an axis transverse to the longitudinal axis A of the handle 706 in a direction 734. The beveled gear 724, as shown in FIG. 7, is offset laterally from the longitudinal axis A of the handle 706. The coaxial gear 726 is positioned proximally of the beveled gear 722 and along the longitudinal axis A of the handle 706, and it is operatively coupled to the beveled gear 724 via a shaft 735 such that it rotates in a direction 736 about an axis transverse to the longitudinal axis A of the handle 706 as a result of rotation of the beveled gear 724.

It should be appreciated that the second coupling 714 can additionally or alternatively include a rack-and-pinion system, worm gears, and/or any other types of connecting mechanisms configured to transfer the movement of the actuating knob 710 to the proximal movement along the longitudinal axis A of the handle 706, as the described techniques are not limited to any specific types of mechanisms included in the second coupling 714.

The gear system 718 of the second coupling 714 engages the guidewire 707 so that the actuation of the gear system 718 (e.g., movement of the gears 722, 724, 726) causes the guidewire 707 to retract proximally. In the illustrated embodiment, as shown in FIG. 7, the gear system 718 is configured to frictionally engage the guidewire 707 by the coaxial gear 726 such that rotational movement of the gear 726 causes the guidewire 707 to retract proximally. However, as one skilled in the art will appreciate, the gear system 718 can moveably engage the guidewire 707 in any suitable manner. For example, it can engage the guidewire 707 by a rack-and-pinion, worm-gear, or any other connection so that moving the actuating knob 710 ultimately causes the guidewire 707 to be retracted proximally. Furthermore, it should be appreciated that the guidewire 707 can be locked to any other component of the handle 706 using a suitable mechanism.

The actuating knob 710 can have a variety of configurations. For example, it can be a dial, a thumbwheel, or it can have any other configuration.

The actuator mechanism 708 of the joint access device 700 is configured so that actuating the actuating knob 710 by a surgeon causes the first coupling 712 to rotate in a first direction and, at the same time, causes one or more of the components of the second coupling 714 to rotate in a second direction. The rotation of the first coupling 712 causes the dilator assembly 702 distally coupled thereto to rotate and advance distally into the interior of a hip or other joint, as shown schematically by an arrow 730 in FIG. 7. Simultaneously or substantially simultaneously with causing the dilator assembly 702 to advance distally, the actuation of the actuating knob 710 causes the components of the second coupling 714, such as gears 722, 724, 726, to move in cooperation to thereby engage the guidewire 707 and retract it proximally simultaneously or substantially simultaneously with distally advancing the dilator assembly 702.

It should be appreciated that the joint access device 700 can have a variety of configurations such that the guidewire 707 is retracted proximally simultaneously or substantially simultaneously with distal advancement of the dilator assembly 702. For example, in some embodiments, the joint access device 700 can include a turnbuckle or any other connection that causes the guidewire 707 to retract proximally simultaneously or substantially simultaneously with distally advancing the dilator assembly 702 in response to actuating the actuator mechanism 708.

FIGS. 8A to 8F illustrate a method of using a joint access device 820 (e.g., device 100 or 700) in accordance with some embodiments to create access to a hip joint 800 for hip arthroscopy. The hip joint 800 comprises a femoral head 802 on a femur 804 which is received within an acetabulum 806. A labrum 808 is a ring of cartilage which surrounds the acetabulum 806. A hip capsule 810 of fibrous tissue encloses the hip joint 800 extending from the acetabulum 806 to the neck 812 of the femur 804 (including connections on the greater trochanter) to stabilize the joint. The capsule 810, formed of tough and fibrous tissue to protect the hip joint 806, can be difficult to penetrate surgically. The joint access device in accordance with the described techniques can facilitate accessing the hip joint through the tough tissue of the capsule to a surgical site within the interior of the hip joint. In particular, the joint access device allows a surgeon to create an access pathway to the interior of the hip joint in a controlled manner, while retracting the guidewire from the surgical site, so that a possibility of damage to the articular cartilage by the distal tip of the device and/or the guidewire is decreased or eliminated.

As shown in FIG. 8A, to access the hip joint 800 in preparation for arthroscopic surgery, a needle 801 (e.g., a cannulated needle) is inserted into the hip joint 800 in a desired access orientation under suitable visualization (e.g., fluoroscopy, X-ray, and/or other known guidance systems). A trajectory of the insertion of the needle 801 is selected so as to establish a pathway to a surgical site. As also shown in FIG. 8A, the needle 801 is typically inserted to a joint under distraction such that it enters a gap between the femoral head 802 and the labrum 808. The guidewire 807 is then be passed through the needle 801 and advanced to a location within the hip joint 800 as schematically shown FIG. 8B where a distal tip 807b of the guidewire 807 protrudes from a distal end of the needle 801. The guidewire 807 can be positioned within the capsule 810, or it can be advanced a desirable distance into the hip joint 800, as shown by way of example in FIG. 8B. The described techniques are not limited to any specific location of the guidewire 807 within the hip joint 800, as the guidewire 807 can be advanced to any position within the hip joint 800 to create an initial pathway to the surgical site.

One skilled in the art will appreciate that the guidewire 807 can be inserted into the hip joint 800 using any suitable technique. As an additional or alternative exemplary technique, the guidewire 807 can have a sharp distal tip so that it can be advanced into the joint without the use of a needle. The guidewire 807 can be inserted into the joint while being mated to a removable handle (not shown), or without the handle.

After the guidewire 807 is advanced distally to a proper location within the hip joint 800, the needle 801 is removed, as schematically illustrated in FIG. 8C where the needle 801 is not shown. The guidewire 807 remains within the hip joint 800.

As shown in FIG. 8D, the joint access device 820, including a dilator assembly 822 and a handle 824 removably coupled thereto, is advanced over the guidewire 807 and inserted in the hip joint 800. Like devices 100 and 700, the joint access device 820 is cannulated such that the guidewire 807 extends therethrough. Components of the joint access device 820 can be assembled together as the device 820 is being advanced over the guidewire 807, or it can be preassembled.

The joint access device 820 is advanced over the guidewire 807 to a first position 809A, until it reaches the outside of the hip capsule 810. In one embodiment, the joint access device 820 is advanced over the guidewire 807 until a distal tip 823 of the device 820 is positioned at the outer surface of the hip capsule 810. In general, the joint access device 820 is advanced over the guidewire 807 such that a distance between the distal tip 807b of the guidewire 807 and the distal tip 823 of the device 820 is any suitable distance sufficient to then advance the device 820 distally over the guidewire 807. The distance can be selected based on a patient's anatomy, a type of damage to the hip joint, and/or any other factors. Furthermore, in some embodiments, the joint access device 820 is advanced so that the distal tip 823 of the device 820 is flush with the distal tip 807b of the guidewire 807.

A surgeon advances the joint access device 820 over the guidewire 807 until he or she receives a tactile impression that the device 820 is positioned against the hip capsule 810. At that point, a further advancement deeper into the joint 800 typically requires a plunging forward action to pass through tight tissue in the hip capsule 810. As mentioned above, such a movement can be difficult to control. Moreover, because of the anatomy of the hip joint, the guidewire is inserted therein at an angle that makes it challenging to insert a sheath or cannula over the guidewire so that it is aligned therewith. Thus, unintentional damage may be caused to the articular cartilage of the femoral head and/or acetabulum. A trauma to the joint can also result from the tip of a guidewire breaking when the dilator is pushed with excessive force into the joint, causing the guidewire to be pinned between the acetabulum and the tip of the dilator.

After the joint access device 820 is advanced over the guidewire 807 to the first position 809A, the guidewire 807 is reversibly locked to the handle 824 in a suitable manner. The handle 824 includes first and second couplings, of which only the second coupling 826 is visible in FIGS. 8D and 8E. It should be appreciated that the second coupling 826 is shown in FIGS. 8D and 8E by way of example only, and in embodiments in which the joint access device 820 is a device similar to that of the device 700 of FIG. 7, the second coupling 826 (e.g., the gear system 718 in FIG. 7) can include one or more components disposed within the handle 824.

Regardless of the configuration of the second coupling 826, the guidewire 807 can be reversibly locked to the second coupling 826 by a suitable locking mechanism (e.g., a locking mechanism 828 in FIG. 8D) so as to fix the position of the guidewire 807 with respect to the second coupling 826. Thus, when the second coupling 826 is moved proximally (or when one or more of its components is moved as in the gear system 718 in FIG. 7), the guidewire 807 is also moved or retracted proximally. As discussed above, the handle 824 can include an actuator (e.g., a push button, lever, etc.) configured to conveniently operate the locking mechanism 828 during the use of the joint access device 820.

After the guidewire 807 is locked to the handle 824, an actuator knob 830 of an actuator mechanism associated with the handle 824 (e.g., the actuator mechanism 202 or 708) is actuated to move the first coupling (not shown) to cause the dilator assembly 822 to advance through the capsule 810 from the first position 809A toward a second position 809B within the hip joint 800 to enable surgical tools to be deployed into the hip joint 800. This is schematically shown in FIG. 8E, illustrating that the distal tip 823 of the dilator assembly 822 is advanced deeper into the hip joint 800 as compared to the position of the distal tip 823 shown in FIG. 8D. In one embodiment, after the guidewire 807 is locked to the handle 824, the distal tip 823 of the dilator assembly 822 travels about 10 mm within the hip joint capsule to create a portal pathway for tools and instruments used in the surgery. However, it is understood that the distance being traveled can vary. For example, in some embodiments, the dilator assembly 822 can travel a total distance from about 5 mm to about 30 mm to access the hip joint.

To advance the dilator assembly 822 distally to thus widen the initial pathway created by the guidewire 807, the actuator knob 830 of the actuator mechanism is rotated or otherwise moved to cause the first and second couplings of the joint access device 820 to move in opposite directions at the same time. As the dilator assembly 822 is advanced distally toward the second position 809B, the actuation of the actuator knob 830 causes the second coupling 826 with the guidewire 807 coupled thereto to move proximally so that the guidewire 807 is retracted (as indicated by a directional arrow 832) from the hip joint 800 substantially simultaneously with advancing the dilator assembly 822 toward the second position 809B. When a device similar to that of the device 700 of FIG. 7 is utilized, rotating or otherwise moving the actuator knob 830 causes components of a second coupling (e.g., gears 722, 724, 726 of the gear system 718) to move in cooperation to ultimately translate the rotation of the actuator knob 830 into a rotation of the coaxial gear 726 configured to engage and proximally retract the guidewire. Thus, the use of the device 820 in accordance with the described techniques allows a more controlled advancement of the dilator assembly, in a less traumatic manner, such that a possibility of unintentional damage to the tissue (such as articular cartilage) in the hip joint is reduced or eliminated.

As discussed above, the guidewire 807 is retracted at a rate that is substantially the same as a rate at which the dilator assembly 822 is advanced distally. In this way, dilator assembly 822 can be said to "climb over" the guidewire 807 as the dilator assembly 822 is advanced distally into the hip joint 800, which allows eliminating or reducing a possibility of the guidewire 807 being dislocated or broken. Additionally or alternatively, in some embodiments, the guidewire 807 can be retracted at a rate that is different than a rate at which the dilator assembly 822 is advanced.

Accordingly, a pathway of a larger diameter suitable for accommodating various tools being passed to and from the surgical site can be created based on the smaller diameter pathway initially created by the guidewire. For example, an initial relatively narrow path (e.g., from about 1 mm to about 2 mm in diameter) created by the guidewire can be widened to a larger path (e.g., from about 2 mm to about 10 mm in diameter) through the hip joint that can be used to pass suitable tools to and from the surgical site.

After the pathway appropriate for an arthroscopic procedure is created as discussed above, the handle 824 is separated from the dilator assembly 822 and removed, as shown in FIG. 8F. The guidewire 807, which can remain locked to the handle 824, can thus also be removed. The arthroscopic procedure can then be performed on the hip joint 800. Tools such as visualization devices (e.g., an arthroscope, camera, etc.) and devices used to treat the hip joint (e.g., capsulotomy blades, shavers, burrs, ablation devices, suture anchors, etc.) can be delivered to the surgical site through the created pathway to the interior of the hip joint, or through other suitable pathways.

Figure 9:
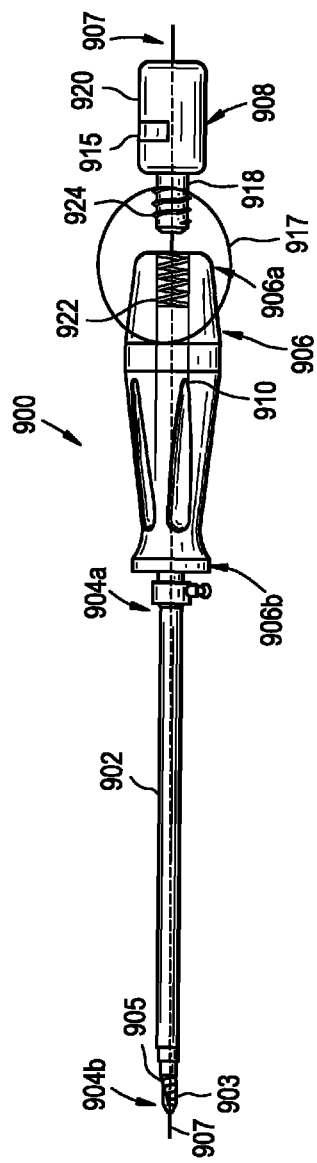
FIG. 9 is a side view of one embodiment of a joint access device.

FIG. 9 illustrates an additional embodiment of a joint access device 900 for a controlled access to the interior space of a joint, such as a hip joint. As shown in FIG. 9, the device 900 includes a dilator assembly 902 having proximal and distal ends 904a, 904b, a distal handle 906 configured to be coupled to the proximal end 904a of the dilator assembly 902, and a proximal handle 908 configured to be coupled to a proximal end 906a of the distal handle 906. It should be appreciated that even through the distal and proximal handles 906, 908 are shown in FIG. 9 as separate components, the distal and proximal handles 906, 908 can be part of the same handle.

The dilator assembly 902 and the distal and proximal handles 906, 908 have respective lumens extending therethrough and in communication with each other such that the joint access device 900 is fully cannulated and receives therein a guidewire 907.

In some embodiments, the dilator assembly 902 can include a sheath or cannula advanced over and removably coupled to a dilator shaft. In other embodiments, the sheath or cannula need not be used. The dilator assembly 902 can be an elongate tubular member with a distally tapered distal end 903. The dilator assembly 902 can have a lumen extending therethrough that receives therein the guidewire 907. As shown in FIG. 9, the dilator assembly 902 is coupled distally to a distal end 906b of the distal handle 906 in a manner similar to that in which the dilator assembly 102 of FIGS. 1, 2 and 4 is coupled to the handle 106.

As shown in FIG. 9, the distal end 904b of the dilator assembly 902 has a thread 905 (e.g., the helical thread 504 or 514 as shown in FIGS. 5A, 5B) formed thereon that facilitate engagement with soft tissue. The thread 905 can have a sharp surface used to cut through and grip the hip capsule. The distal end 904b can include any other surface features that can help in advancing the joint access device 900 into a hip or other joint to create access thereto for larger surgical tools and instruments.

The distal handle 906 can have a variety of configurations. As shown in FIG. 9, the distal handle 906 has a substantially cylindrical shape and is configured to be held by a surgeon. In the illustrated embodiment, the distal handle 906 is configured to reversibly engage with the proximal handle 908 via a threaded connection 917. As shown in FIG. 9, the distal handle 906 has an inner lumen 910 extending therethrough which can be configured to engage (e.g., threadedly) with the proximal handle 908 in a suitable manner. For example, as shown in FIG. 9, the inner lumen 910 has an internal thread 922 formed therein that is configured to engage a respective thread 924 formed on the proximal handle 908. The thread 922 can be a continuous thread or it can include a plurality of threads.

The proximal handle 908 can also have a variety of configurations. As shown in FIG. 9, the proximal handle 908 has a distal connection portion 918 and a proximal grip portion 920 configured to be held by a surgeon. The connection portion 918, which has an outer diameter that is less than a diameter of the grip portion 920, is configured to threadedly engage proximally to the distal handle 906. FIG. 9 illustrates that the connection portion 918 includes an external thread 924 formed on an outer surface thereof which is configured to engage with the internal thread 922 in the inner lumen 910 of the distal handle 906 to thereby reversibly threadedly engage the distal and proximal handles 906, 906. Like the thread 922, the thread 924 can be a continuous thread or it can include a plurality of threads.

Figure 10:
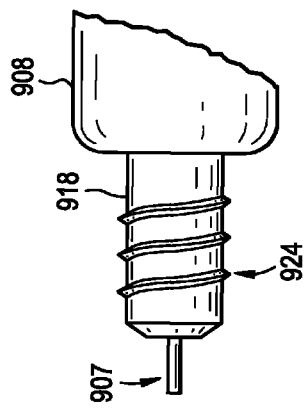
FIG. 10 is a schematic illustration of a threaded connection portion of the device of FIG. 9.

An enlarged view of the connection portion 918 of the proximal handle 908 is shown in FIG. 10. In one embodiment, a pitch of the thread 924 is such that about 720 degrees of rotation of the handle 908 is equivalent to about 8 millimeters (mm) travel through the hip capsule. For example, the pitch of the thread 924 is about 4 mm. The pitch of the internal thread 922 formed in the distal handle 906 is complimentary to the pitch of the thread 924 of the connection portion 918.

It should be appreciated that the threaded connection 917 between the distal and proximal handles 906, 908 is shown by way of example only, and the distal and proximal handles 906, 908 can be connected in any suitable manner. For example, the distal and proximal handles 906, 908 can be connected via a rack-and-pinion, worm-gear, interference-cam connection, or any other connection that allows reversibly coupling the handles 906, 908 to each other.

As mentioned above, the joint access device 900 has a lumen, or more than one lumen in communication with each other, extending along the entire length thereof so that the device 900 is able to receive the guidewire 907 therethrough. The guidewire 907 can be reversibly locked to the proximal handle 908 in any location thereof and in any suitable manner. In the illustrated example, a locking mechanism 915 is configured to lock the guidewire 907 to the grip portion 920 of the proximal handle 908, as schematically shown in FIG. 9. In this way, the guidewire 907 can be moved together with the proximal handle 908.

Regardless of the configuration of the connection between the proximal and distal handles 906, 908 and the way in which the guidewire 907 is coupled to the proximal handle 908, the dilator assembly 902 is advanced distally toward the interior space of a joint (e.g., a hip joint) and the guidewire 907 is retracted at least partially simultaneously with the advancement of the dilator assembly 902.

In use, the guidewire 907 is advanced to a surgical site within a hip joint and the joint access device 900 is advanced over the guidewire 907 to a first position within the hip joint. The guidewire 907 is then locked to the proximal handle 908, for example, using the locking mechanism 915.

In general, the joint access device 900 can be operated to provide access to the interior space of a joint, such as hip joint, using a method similar to that shown in connection with FIGS. 8A to 8F for joint access device 820. In some embodiments, the joint access device 900 can be operated using both hands of the surgeon. For example, after the guidewire 907 is locked to the proximal handle 908, the distal handle 906, held by one hand of the surgeon, is moved (e.g., rotated) distally with respect to the proximal handle 908 so as to advance the dilator assembly 902 distally toward a second position within the hip joint. While the distal handle 906 is being rotated using one hand of the surgeon, the surgeon can steadily hold the proximal handle 908 (e.g., by the grip portion 920) in another hand so that a position of the proximal handle 908 remains fixed. In this way, as the distal handle 906 moves to cause the dilator assembly 902 to advance distally, the position of the proximal handle 908 with respect to the distal handle 906 remains substantially the same and the guidewire 907, locked to the proximal handle 908, stays in a fixed position. As a result, as the dilator assembly 902 is advanced distally, the guidewire 907 is simultaneously or substantially simultaneously retracted proximally.

Additionally or alternatively, the surgeon can hold the grip portion 920 of the proximal handle 908 and, rather than holding the proximal handle 908 steady, can move (e.g., rotate) the proximal handle 908 away from the distal handle 906 so that the connection portion 918 of the proximal handle 908 is retracted from the proximal end 906a of the distal handle 906. In this way, the guidewire 907 is retracted from the surgical site.

The distal and proximal handles 906, 908 can be configured such that the guidewire 907 is retracted at a rate that is substantially the same as a rate at which the dilator assembly 902 is advanced distally. However, in some embodiments, the guidewire 907 is retracted at a rate that is different than the rate of advancement of the dilator assembly 902. The rate at which the guidewire 907 can be retracted depends on a configuration and size of the thread 924 formed on the connection portion 918, the thread 905 formed on the distal end 904b of the dilator assembly 902, and/or any other suitable features of the device 900.

It should be appreciated that although illustrated embodiments provide techniques for providing access to a hip joint for arthroscopy, the techniques can be adapted for providing access to interior spaces of a shoulder, knee, ankle, wrist, elbow, eye, or for any other uses.

What is claimed is:
1. A surgical method for accessing an interior space of a joint, comprising:
  advancing a guidewire into the joint capsule;
  advancing a cannulated dilating instrument over the guidewire toward the joint capsule to a first position outside the joint capsule , the dilating instrument being coupled at a proximal end thereof to a handle such that the dilating instrument is configured for moving relative to the handle;

reversibly locking the guidewire within the handle when the dilating instrument is in the first position; and actuating an actuator on the handle to:

cause the cannulated dilating instrument to advance distally from the first position toward a second position within the joint capsule, and cause the guidewire to retract proximally with respect to the joint capsule simultaneously with advancing the dilating instrument toward the second position.

2. The method of claim 1, wherein the handle has first and second couplings disposed therein.

3. The method of claim 2, wherein actuating the actuator comprises:

moving the first coupling to cause the dilating instrument to advance distally from the first position toward a second position within the joint capsule; and moving the second coupling to cause the guidewire to retract proximally simultaneously with advancing the dilating instrument toward the second position.

4. The method of claim 2, wherein reversibly locking the guidewire comprises locking the guidewire to the second coupling.

5. The method of claim 2, wherein the second coupling is configured to be operably coupled to the guidewire and to be moved by rotation.

6. The method of claim 2, wherein the actuator includes a first engaging component operatively coupled to the first coupling and a second engaging component operatively coupled to the second coupling.

7. The method of claim 6, wherein the first engaging component is operatively coupled to the first coupling via a first threaded connection.

8. The method of claim 6, wherein moving the first engaging component causes the first coupling to move in a first direction and moving the second engaging component causes the second coupling to move in a second direction that is opposite to the first direction.

9. The method of claim 1, wherein a rate of retracting the guidewire is substantially the same as a rate of advancing the dilating instrument.

10. The method of claim 1, wherein a rate of retracting the guidewire is different than a rate of advancing the dilating instrument.

11. The method of claim 1, wherein a distal tip of the dilating instrument has a cutting thread.

12. The method of claim 1, wherein the joint comprises a hip joint capsule.

\* \* \* \* \*